(12) United States Patent
Miyajima et al.

(10) Patent No.: US 7,378,551 B2
(45) Date of Patent: May 27, 2008

(54) AMIDE COMPOUND

(75) Inventors: Tetsuya Miyajima, Wakayama (JP);
Takeshi Ihara, Wakayama (JP);
Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/591,468

(22) PCT Filed: Feb. 21, 2005

(86) PCT No.: PCT/JP2005/002700
§ 371 (c)(1), (2), (4) Date: Sep. 1, 2006

(87) PCT Pub. No.: WO2005/082839
PCT Pub. Date: Sep. 9, 2005

(65) Prior Publication Data
US 2007/0185208 A1    Aug. 9, 2007

(30) Foreign Application Priority Data
Mar. 1, 2004    (JP) .............................. 2004-056401
Nov. 22, 2004    (JP) .............................. 2004-336923

(51) Int. Cl.
C07C 233/05    (2006.01)
A61K 9/14    (2006.01)
A61K 31/65    (2006.01)

(52) U.S. Cl. ...................... 564/153; 514/616; 424/484; 424/DIG. 5

(58) Field of Classification Search ................ 564/153; 514/616; 424/484, DIG. 5
See application file for complete search history.

(56) References Cited

U.S. PATENT DOCUMENTS 5,776,494 A * 7/1998 Guskey et al. .............. 424/414
6,410,478 B1 * 6/2002 Torii et al. .................. 503/201

FOREIGN PATENT DOCUMENTS

JP    7 309821    11/1995

JP    2001 146075    5/2001
JP    2001 507689    6/2001

OTHER PUBLICATIONS

Lee et al, J. Med. Chem., 28(3), pp. 317-323, 1985.*

* cited by examiner

*Primary Examiner*—Shailendra Kumar
(74) *Attorney, Agent, or Firm*—Oblon, Spivak, McClelland, Maier & Neustadt, P.C.

(57) ABSTRACT

A gelling agent having a high ability of gelling an oily base which is capable of giving a gel composition having a strong gel strength and a good transparency, a gel composition having a strong gel strength and a good transparency, an external composition having a good feel upon use, a cosmetic preparation having a good feel upon use, and a fragrance composition having a good transparency and a good appearance is provided. An amide compound represented by the following formula 1:

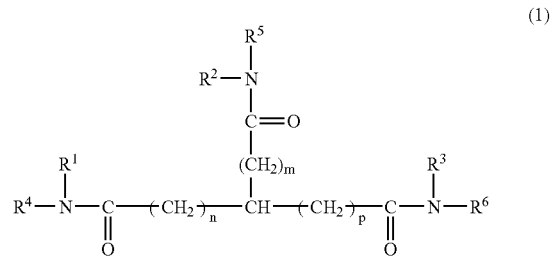

is used. In formula 1, $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom. $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group; and m, n and p are each independently an integer of from 0 to 3.

6 Claims, 7 Drawing Sheets

AMIDE COMPOUND

This application is a 371 of PCT/JP05/20700, filed Feb. 21, 2005.

TECHNICAL FIELD

The present invention relates to novel amide compounds and further relates to gelling agents, gel compositions, external compositions, cosmetic preparations, and fragrance compositions each containing the amide compound.

BACKGROUND ART

As a low-molecular weight gelling agent for oily bases, 12-hydroxystearic acid, condensates of an aromatic aldehyde and a polyhydric alcohol such as dibenzylidene-D-sorbitol, and N-lauroyl-L-glutamic acid dibutylamide have been conventionally known, and cosmetic preparations containing such a substance as the gelling agent have been reported (for example, Patent Document 1).

Of the above gelling agents, dibenzylidenesorbitol is effective only for gelatinizing highly polar oily bases such as polyols. Therefore, cosmetic preparations made of a gel composition which is prepared using such a gelling agent unfavorably provide a strong sticky feel upon its application. The gel compositions prepared using the other gelling agents mentioned above fail to have sufficient gel strength because of their poor compatibility and being nonhomogenous. Therefore, a gel composition prepared as a cosmetic preparation for skin application easily loses its form likely caused by the problem of strength. In addition, the gel compositions prepared from the above gelling agents and oily base are all white in color with a low transparency, which makes the compositions unfavorable in view of its aesthetical appearance.

As a high-molecular weight gelling agent, on the other hand, polyamides have been known and cosmetic preparations containing such polyamides have been proposed (for example, Patent Document 2).

However in case, cosmetic preparations are made using a gel composition which is prepared using such a high-molecular weight gelling agent, it is difficult to be made into the form of a stick, etc. because of their poor strength and they are less spreadable upon application due to their high viscosity.

[Patent Document 1] JP 51-19139A
[Patent Document 2] JP 2002-60330A

DISCLOSURE OF THE INVENTION

Problems to be Solved by the Invention

The present invention relates to a novel amide compound useful as a gelling agent having a high ability to gelatinize oily bases, gel strength and transparency, and further relates to a gel composition, an external composition, a cosmetic preparation, and a fragrance composition which acquire a high ability to gelatinize oily bases, gel strength and transparency by the inclusion of the amide compound.

Means for Solving the Problems

The present invention provides:
(1) An amide compound represented by the following formula 1:

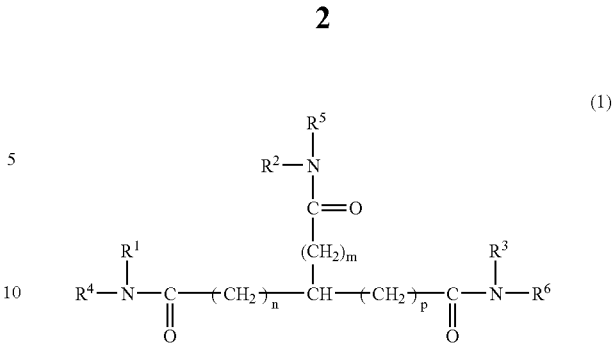

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group; and m, n and p are each independently an integer of from 0 to 3;
(2) A gelling agent containing the amide compound described in paragraph 1;
(3) A gel composition containing an oily base and the gelling agent described in paragraph 2;
(4) An external composition containing the amide compound described in paragraph 1;
(5) A cosmetic preparation containing the amide compound described in paragraph 1; and
(6) A fragrance composition containing the amide compound described in paragraph 1.

Effect of the Invention

According to the present invention, there are provided a novel amide compound useful as a gelling agent for oily bases; a gelling agent containing the amide compound having a high ability of gelatinizing oily bases; a gel composition having a strong gel strength and good transparency; a stable cosmetic preparation having a good feel upon use; a stable external composition having a good feel upon use; and a long-lasting fragrance composition having a strong gel strength, good transparency and good aesthetical appearance, each being applicable to the cosmetic field, etc.

BEST MODE FOR CARRYING OUT THE INVENTION

Figure 1:
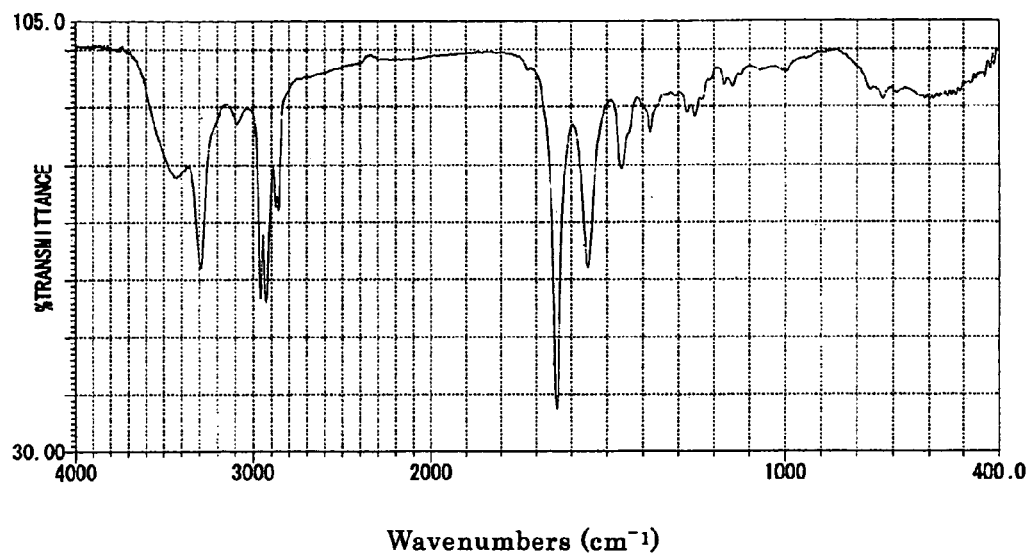
FIG. 1 is an IR chart of the amide compound A obtained in Example 1.

The inventors have found that an amide compound having a specific structure meets the above objects as a gelling agent for oily bases. It has been further found that a gel composition prepared from such amide compound and oily base has a strong gel strength and good transparency, and that the gel composition has enough strength to be used in cosmetic preparations which is easily applied to skin when made into the form of a stick, etc.

The amide compound of the present invention is represented by the above formula 1. In formula 1, $R^1$, $R^2$ and $R^3$ are each independently a hydrogen atom or an alkyl group having 1 to 3 carbon atoms with the proviso that at least one of $R^1$, $R^2$ and $R^3$ is a hydrogen atom. Preferably, two or more of $R^1$, $R^2$ and $R^3$ are hydrogen atoms. The alkyl group having 1 to 3 carbon atoms may include a methyl group, ethyl group, propyl group, and isopropyl group, with a methyl group being preferred. $R^1$, $R^2$ and $R^3$ may be the same or different from one another.

$R^4$, $R^5$ and $R^6$ are each a saturated or unsaturated, linear or branched hydrocarbon group having a total carbon number of from 6 to 24, preferably from 8 to 24, and more preferably from 12 to 24, which optionally has at least one group selected from the group consisting of an ether group, amide group, ester group, amino group and hydroxyl group.

Examples of the linear saturated hydrocarbon group include hexyl, heptyl, octyl, nonyl, decyl, undecyl, dodecyl, tridecyl, tetradecyl, pentadecyl, hexadecyl, heptadecyl, octadecyl, icosyl, docosyl, and tetracosyl.

The position of the branch in the branched saturated hydrocarbon group is not limited, and examples thereof include methylpentyl, methylhexyl, ethylhexyl, methylnonyl, dimethyloctyl, tetramethyloctyl, methyldodecyl, dimethylundecyl, trimethyldecyl, hexyldecyl, methylpentadecyl, dimethyltetradecyl, trimethyltridecyl, tetramethyldodecyl, octyldodecyl, and decyltetradecyl.

The position of the unsaturated bond in the linear or branched, unsaturated hydrocarbon group is not limited, and examples thereof include hexenyl, octenyl, decenyl, dodecenyl, tetradecenyl, hexadecenyl, octadecenyl, icosenyl, docosenyl, tetracosenyl, methylpentenyl, methylhexenyl, ethylhexenyl, methylnonenyl, dimethyloctenyl, and tetramethyloctenyl.

The position of the hydroxyl group in the linear or branched, saturated hydrocarbon group having a hydroxyl group is not limited, and examples thereof include hydroxyhexyl, hydroxyoctyl, hydroxydecyl, hydroxydodecyl, hydroxytetradecyl, hydroxyhexadecyl, hydroxyoctadecyl, hydroxyicosyl, hydroxydocosyl, hydroxytetracosyl, hydroxymethylpentyl, hydroxymethylhexyl, hydroxyethylhexyl, hydroxymethylnonyl, hydroxydimethyloctyl, and hydroxytetramethyloctyl.

The positions of the hydroxyl group and unsaturated bond in the linear or branched, unsaturated hydrocarbon group having a hydroxyl group are not limited, and examples thereof include hydroxyhexenyl, hydroxyoctenyl, hydroxydecenyl, hydroxydodecenyl, hydroxytetradecenyl, hydroxyhexadecenyl, hydroxyoctadecenyl, hydroxyicosenyl, hydroxydocosenyl, hydroxytetracosenyl, and hydroxymethylpentenyl.

Examples of the hydrocarbon group having an ether group include (ethylhexyloxy)ethyl, dodecyloxyethyl, octadecyloxyethyl, octadecyloxypropyl, [(octadecyloxy)ethyloxy]ethyl, and octadecenyloxypropyl.

Examples of the hydrocarbon group having an amide group include N-octadecyloylaminoethyl, N-dodecyloylaminopropyl, N-octadecenyloylaminopropyl, and N-(2-ethylhexanoyl)aminoethyl.

An example of the hydrocarbon group having an ester group includes 2-stearoyloxyethyl, and an example of the hydrocarbon group having an amino group includes N,N-dioctyl-3-aminopropyl.

In view of the transparency and strength of the gel to be formed by the amide compound, the hydrocarbon group for each of $R^4$, $R^5$ and $R^6$ is preferably the saturated or unsaturated, linear or branched hydrocarbon group having from 8 to 24 carbon atoms or the hydrocarbon group having an ether group mentioned above, more preferably the saturated or unsaturated, linear or branched hydrocarbon group having from 8 to 22 carbon atoms, and particularly preferably octadecyloxyethyl and octadecyloxypropyl.

In formula 1, m, n and p are each independently an integer of from 0 to 3. In view of imparting a transparent appearance to the gel, m, n and p are preferably different from one another, more preferably m is 1 or 2 and/or p is 2 or 3, and particularly preferably m is 1, n is 0 and p is 2, or m is 2, n is 0 and p is 3.

The amide compound having such a structure is produced by any method without particular limitation as far as the amide compound having the structure mentioned above can be produced. For example, the amide compound is produced by the following method.

The amide compound represented by formula 1 may be produced by the reaction of the alkanetricarboxylic acid represented by the following formula 2:

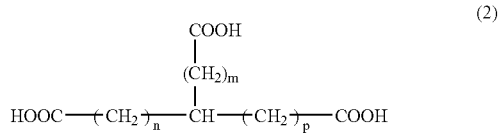

(2)

wherein m, n and p are the same as above, or its derivative and amine compounds are each represented by the following formula 3-a, 3-b, or 3-c:

(3-a)

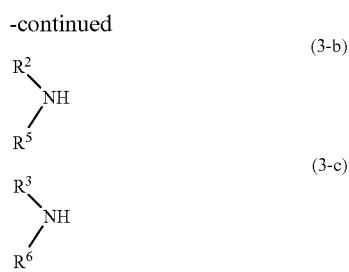

(3-b)

(3-c)

wherein $R^1$ to $R^6$ are the same as above.

The amine compounds each represented by formula 3-a, 3-b or 3-c may be the same or different from one another, and at least one thereof is preferably a primary amine.

The derivative of the alkanetricarboxylic acid represented by formula 2 may include compounds derived from the alkanetricarboxylic acid by converting at least one carboxylic group to a lower alkyl ester group, acid halide group or acid anhydride group. In the present invention, the alkanetricarboxylic acid is advantageously used in the free acid form.

To produce the amide compound of the present invention in high yields, the amine compounds of formula 3-a, 3-b and 3-c are preferably used in excess of the stoichiometric amount with respect to the alkanetricarboxylic acid of formula 2. The amine compound is generally used in an amount of from 3 to 10 mol, preferably from 3 to 6 mol per one mole of the alkanetricarboxylic acid.

The reaction is carried out generally at from 120 to 220° C. The reaction time depends on the reaction temperature and the types of the alkanetricarboxylic acid and amine compounds as raw materials, and therefore, is not determined absolutely, but generally is from about 1 to about 20 hours.

In addition to the amide compound, the gelling agent of the present invention may further contain a known gelling agent for oily bases. If such a known gelling agent is used, the content of the amide compound in the gelling agent is preferably at least 30% by weight in view of imparting the strength, stability and transparent appearance to the gel. Examples of known gelling agents for oily bases include 12-hydroxystearic acid condensates of aromatic aldehyde and polyhydric alcohol such as dibenzylidene-D-sorbitol; N-lauroyl-L-glutamic acid dibutylamide disclosed in JP 51-19139A; and silicones such as polyoxyalkylene-modified organopolysiloxane disclosed in JP 61-113646A, dihydrolanosterol disclosed in JP 3-6283A, alkoxyalkylpolysiloxane disclosed in JP 11-35826A and siloxane polymer including a segment of amino acid derivative disclosed in JP 2002-80599A.

The gelling agent may further contain, according to its purpose and need, water, a surfactant, a water gelling agent, and other additives.

The surfactant may be any of anionic surfactants, nonionic surfactants, cationic surfactants, and amphoteric surfactants. Examples of the anionic surfactant include the salt of an alkylsulfuric acid, the salt of alkylpolyalkylene oxide sulfate, the salt of alkyl phosphate, the salt of a fatty acid, the salt of N-(long acyl)amino acid, the salt of dialkyl sulfosuccinate, and the salt of alkyl ether carboxylate.

Examples of the nonionic surfactants include alkylpolyalkylene oxide, sorbitan fatty acid ester, sucrose fatty acid ester, alkyl glucoside, mono- or polyglycerol fatty acid ester, glycerol alkyl ether, alkylpolyalkylene oxide glycerol ether, alkanolamide of fatty aid, and alkylamine oxide.

Examples of the cationic surfactants include alkylammonium chloride, dialkylammonium chloride, their quaternary ammonium salt, benzalkonium salt, and fatty acid acylarginine ester.

Examples of the amphoteric surfactants include betaine-type surfactants such as carboxy betaine, aminocarboxylic acid-type surfactants, and imidazoline-type surfactants.

Examples of the water gelling agent include cross-linked polycarboxylic acid salts and hydrophobic polysaccharide derivatives.

Other additives may include amino acids such as glycine, alanine, serine, threonine, arginine, glutamic acid, aspartic acid, leucine, and valine; polyhydric alcohols such as glycerol, ethylene glycol, 1,3-butylene glycol, and propylene glycol; water-soluble polymers such as polyamino acid including polyglutamic acid and polyaspartic acid, salts of polyamino acid, polyethylene glycol, gum arabic, alginic acid salts, xanthane gum, hyaluronic acid, salts of hyaluronic acid, chitin, chitosan, water-soluble chitin, carboxyvinyl polymer, carboxymethylcellulose, hydroxyethylcellulose, hydroxypropyltrimethylammonium chloride, polychlorodimethylmethylenepiperidium, quaternary ammonium salt of polyvinylpyrrolidone derivative, cationic protein, decomposition product of collagen and its derivative, acylated protein, and polyglycerol; sugar alcohol such as mannitol and its alkylene oxide adduct; and lower alcohols such as ethanol and propanol. Also usable are animal or vegetable extracts, intercellular lipids such as ceramide, nucleic acids, vitamins, enzymes, anti-inflammatory agents, disinfectants, preservatives, antioxidants, ultraviolet absorbers, chelating agents, antiperspirants, pigments, colorants, oxidation dyes, organic or inorganic powders, pH adjustors, pearly pigments, wetting agents, and fragrances.

The gel composition of the present invention contains an oily base and the above gelling agent. The oily base is not limited to a particular type as far as it can sufficiently dissolve the gelling agent by heating and form a gel upon cooling to room temperature. Examples of the oily bases include silicone oil, higher alcohols , cetyl alcohol, isostearyl alcohol, lauryl alcohol, hexadecyl alcohol, and octyldodecanol; fatty acids such as isostearic acid, undecylenic acid and oleic acid; esters such as myristyl myristate, hexyl laurate, decyl oleate, isopropyl myristate, hexyldecyl dimethyloctanoate, glycerol monostearate, diethyl phthalate, ethylene glycol monostearate, and octyl oxystearate; hydrocarbon compounds such as liquid paraffin, vaseline, squalane, and squalene; waxes such as lanolin, hydrogenated lanolin and carnauba wax; oil and fat such as coconut oil, palm kernel oil, camellia oil, sesame oil, castor oil, and olive oil; fragrances such as pinene, limonene, terpinolene, geraniol, citronellol, menthol, citral, citronellal, vanillin, undecalactone, methylnonyl ketone, pulegone, nootkatone, coumarin, muscone, cyclopentadecanone, and cyclopentadecanolide.

These oily bases may be used alone or in combination.

Examples of the silicone oils include ether-modified silicones such as methylpolysiloxane, high-polymerization degree methylpolysiloxane, polyoxyethylene-methylpolysiloxane copolymer, and polyoxypropylene-methylpolysiloxane copolymer; stearoxymethylpolysiloxane, stearoxytrimethylsilane, methylhydrogenpolysiloxane, octamethylpolysiloxane, cyclic silicones such as decamethylcyclopentasiloxane, octamethylcyclotetrasiloxane, tetrahydrotetramethylcyclotetrasiloxane, methylcyclopolysiloxane, and dodecamethylcyclohexasiloxane;

methylphenylpolysiloxane, trimethylsiloxysilicic acid, amino-modified silicones such as aminoethylaminopropylsiloxane-dimethylsiloxane copolymer; silanol-modified polysiloxanes; alkoxy-modified polysiloxanes; fatty acid-modified polysiloxanes; fluorine-modified polysiloxanes; epoxy-modified polysiloxanes; alkoxy- modified polysiloxane perfluoropolyether; polyvinyl acetate dimethylpolysiloxane; and mixtures thereof.

Of the above oily bases, silicone oils, esters, hydrocarbon compounds, fatty oil, hydroxyl group-free fragrances recited above, and mixtures thereof are preferred in view of the strength and transparency.

The content of the gelling agent in the gel composition of the present invention is preferably from 0.1 to 10% by weight when expressed by the amount of the amide compound in view of imparting the strength, stability and transparent appearance to the gel. The content of the oily base is generally selected from the range of from 10 to 99.9% by weight. If the content of the oily base is within the above range, a good gel strength is obtained. The content of the oily base is preferably from 20 to 99% by weight.

The gel composition of the present invention is produced by any method without specific limitation, for example, by heating a mixture of an oily base and a gelling agent at about 50 to about 180° C. while stirring until a uniform solution is formed, and then, cooling the resultant solution.

Each of the external composition, cosmetic preparation and fragrance composition of the present invention contains the gelling agent or gel composition of the invention. The external composition, cosmetic preparation and fragrance composition may contain, if necessary, the known gelling agent, oily base, surfactant, and other additives, each described above. These are blended with the gel composition before its preparation, during its preparation, after its preparation or in all these stages. The production method of each composition is not limited, and a method generally usable in cosmetic art, such as a mixing method, a stirring method and a kneading method, may be employed.

The form of the external composition, cosmetic preparation and fragrance composition of the present invention is not particularly limited, and may include, in addition to a solid form, a uniform cream containing the gelling agent and a solution or cream in which the gel composition is dispersed. These forms may contain another component conventionally used, for example, oil agents, purified water, surfactants of various types, wetting agents, preservatives, antioxidants, fragrances, powders, intercellular lipids such as ceramide, ultraviolet absorbers, and medicinal substances.

The content of the gelling agent in the external composition is preferably from 0.1 to 10% by weight except that the gelling composition is dispersed in the external composition. A stable gel is formed when the content is 0.1% by weight or more, and a transparent appearance and a good feel upon use are attained when it is 10% by weight or less. The above content of the gelling agent corresponds to the content of the amide compound which is preferably from 0.05 to 10% by weight and more preferably from 0.1 to 10% by weight.

When dispersing the gel composition, the dispersed amount is preferably 0.1% by weight or more. This dispersing range is preferred because users can easily conceive the effects of dispersing in both cases of achieving a stable dispersion by gelling functional substances and improving the feel upon use.

The content of the gelling agent of the present invention in each of the cosmetic preparation and fragrance composition is preferably from 0.05 to 10% by weight and more preferably from 0.1 to 10% by weight when expressed by the amount of the amide compound of the invention in view of the stability of forms and transparent appearance.

EXAMPLES

The present invention will be described in more detail with reference to the examples. However, it should be noted that the scope of the present invention is not limited by the following examples and comparative examples.

Example 1

Production of Amide Compound A

Figure 2:
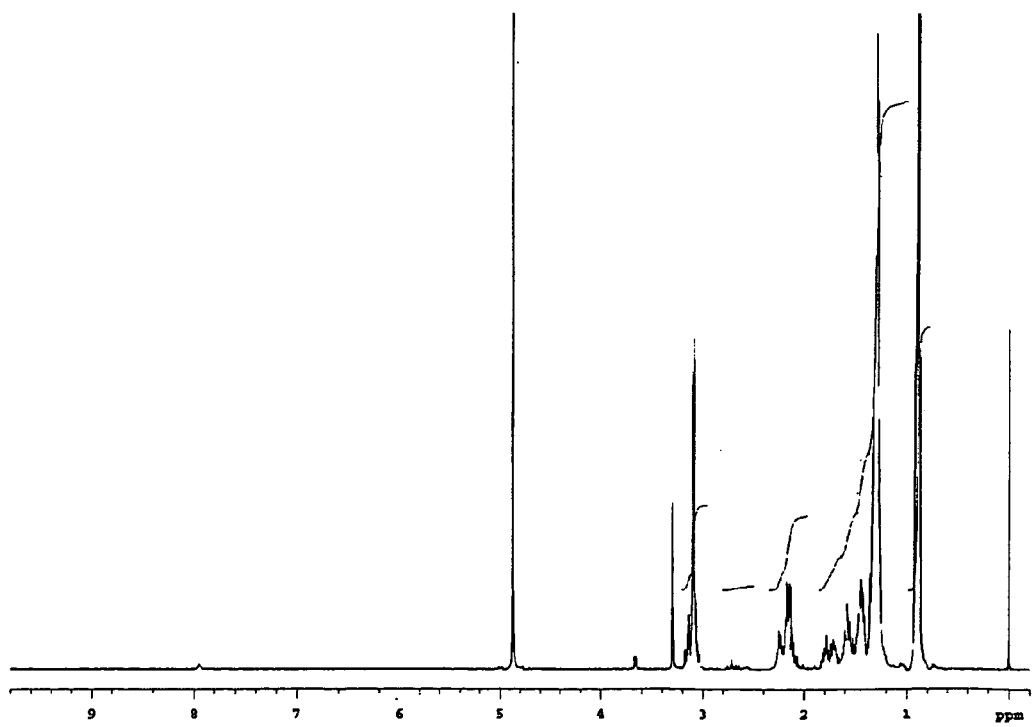
FIG. 2 is a 400 MHz $^1$H-NMR chart of the amide compound A obtained in Example 1.

In a four-necked, round-bottomed 300-mL flask equipped with a dehydration tube, 54.5 g of 2-ethylhexylamine and 15.3 g of hexane-1,3,6-tricarboxylic acid were stirred for 10 hours at 150° C. under a nitrogen stream while removing the water being generated. The excess amine was removed by blowing nitrogen under ordinary pressure at 150° C., and further blowing 100 g of steam under 6.7 kPa at 150° C., to obtain 16 g of amide compound A (hexane-1,3,6-tricarboxylic acid tri-(2'-ethylhexyl)amide) in a brown glassy solid. The yield was 41%. An IR chart and a 400 MHz $^1$H-NMR chart of the obtained compound are shown in FIG. 1 and FIG. 2, respectively. IR was measured by a KBr tablet method and 400 MHz $^1$H-NMR was measured under the conditions: solvent =$CD_3OD/CDCl_3$, internal standard =TMS, and temperature =50° C. The same measuring conditions were used below.

Example 2

Production of Amide Compound B

Figure 3:
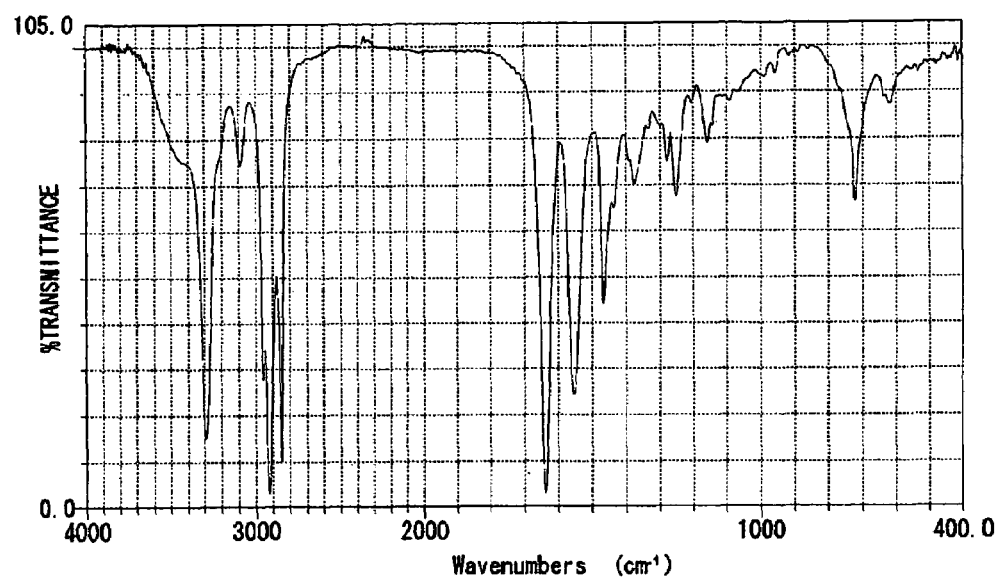
FIG. 3 is an IR chart of the amide compound B obtained in Example 2.
Figure 4:
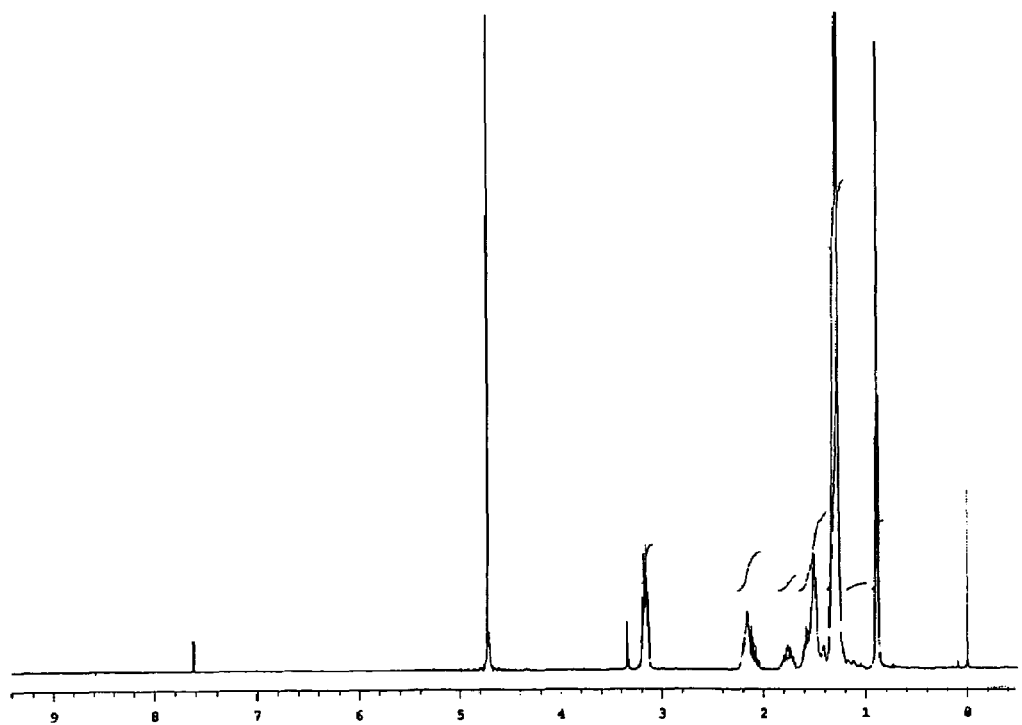
FIG. 4 is a 400 MHz $^1$H-NMR chart of the amide compound B obtained in Example 2.

In a four-necked, round-bottomed 300-mL flask equipped with a dehydration tube, 42.1 g of dodecylamine and 15.0 g of hexane-1,3,6-tricarboxylic acid were stirred for 7 hours at 160° C. under a nitrogen stream while removing the water being generated. After adding 12.7 g of dodecylamine, the product was aged at 165° C. for 8 hours. After further adding 12.7 g of dodecylamine, the aging was continued at 165° C. for 9 hours and at 175° C. Then, after adding 12.7 g of dodecylamine, the ageing was further continued at 175° C. for 8 hours. After confirming the disappearance of the peak attributable to the carboxylic acid (vC=O (carboxylic acid) 1720 cm$^{-1}$) by IR, the product was recrystallized from 2.5 L of ethanol, filtered and dried, to obtain 40.1 g of amide compound B (hexane-1,3,6-tricarboxylic acid tridodecylamide) as a white powdery solid. The yield was 81%. An IR chart and a 400 MHz $^1$H-NMR chart of the obtained compound are shown in FIG. 3 and FIG. 4, respectively.

Example 3

Production of Amide Compound C

Figure 5:
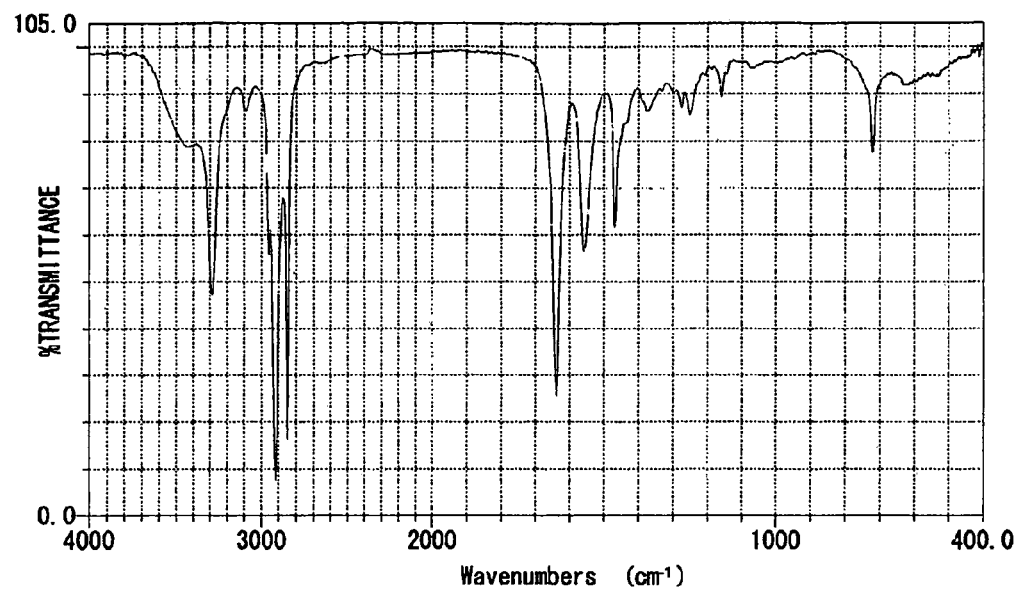
FIG. 5 is an IR chart of the amide compound C obtained in Example 3.
Figure 6:
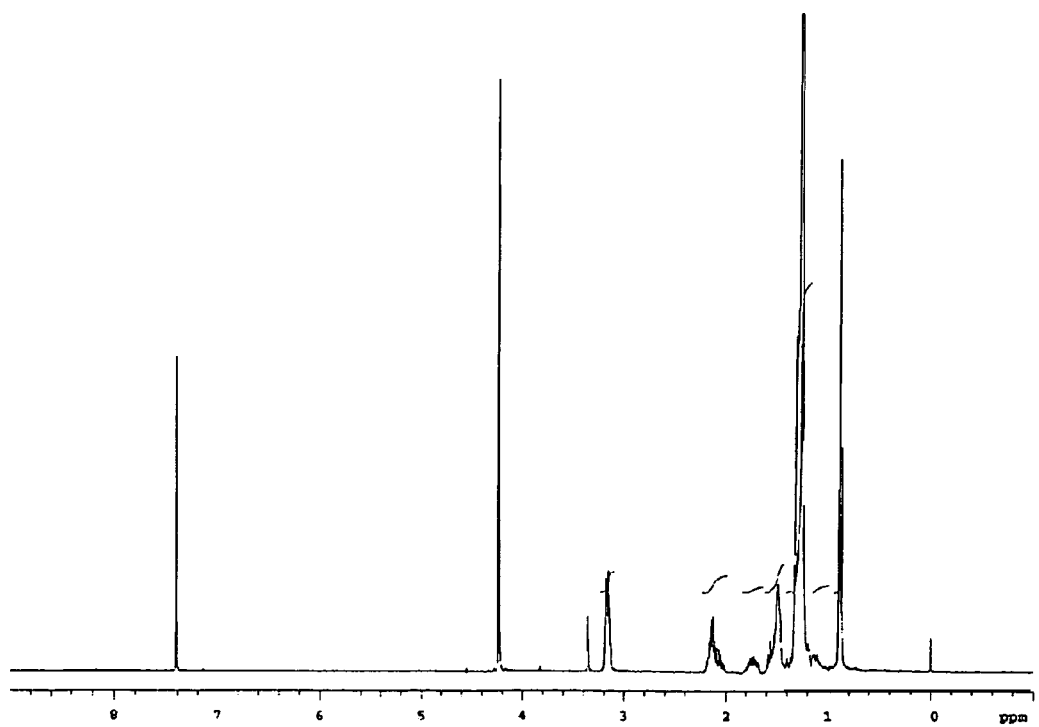
FIG. 6 is a 400 MHz $^1$H-NMR chart of the amide compound C obtained in Example 3.

In a four-necked, round-bottomed 300-mL flask equipped with a dehydration tube, 111.1 g of octadecylamine and 1.5 g of hexane-1,3,6-tricarboxylic acid were stirred for one hour at 165° C. under a nitrogen stream while removing the water being generated. During the ageing at 165° C. for 4.5 hours, 13.5 g of hexane-1,3,6-tricarboxylic acid in total was added in three portions, and the ageing was further continued at 165° C. for an additional 5 hours. After confirming the disappearance of carboxylic acid by IR, the product was recrystallized from a mixed solvent of 4 L of ethanol and 0.6 L of hexane, filtered and dried, to obtain 57.1 g of amide compound C (hexane-1,3,6-tricarboxylic acid trioctadecylamide) as a white powdery solid. The yield was 85%. An IR chart and a 400 MHz $^1$H-NMR chart of the obtained compound are shown in FIG. 5 and FIG. 6, respectively.

Example 4

Production of Amide Compound D

Figure 7:
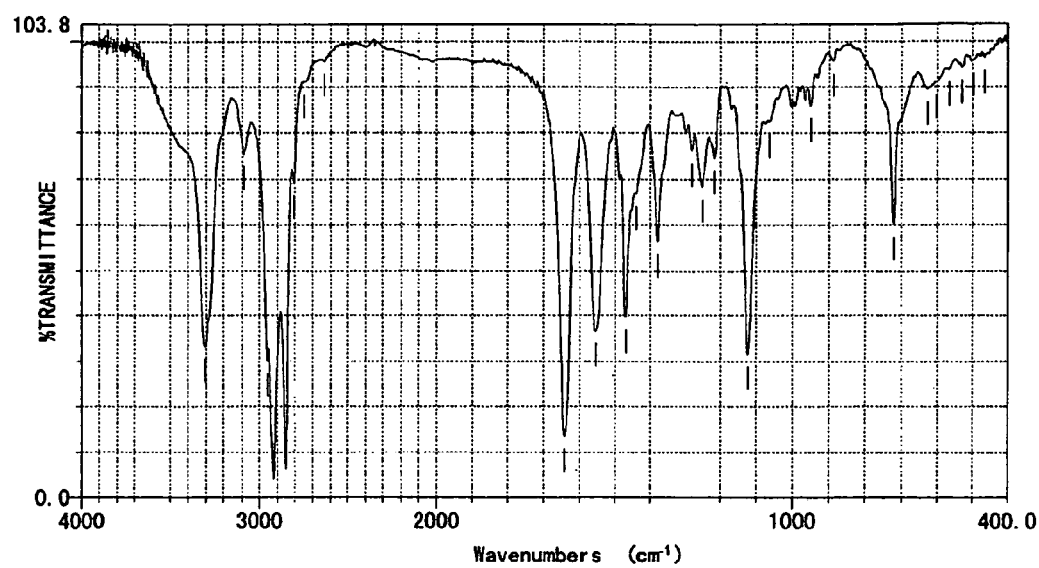
FIG. 7 is an IR chart of the amide compound D obtained in Example 4.
Figure 8:
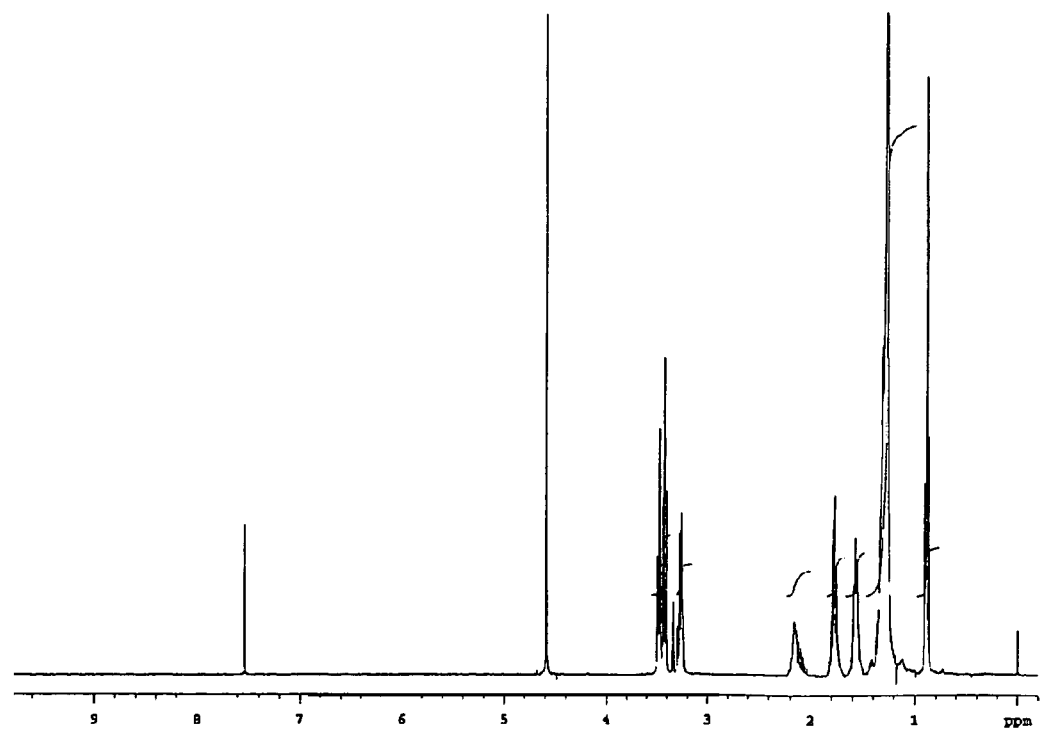
FIG. 8 is a 400 MHz $^1$H-NMR chart of the amide compound D obtained in Example 4.

After charging 67.6 g of 3-octadecyloxypropylamine in a four-necked, round-bottomed 300-mL flask equipped with a dehydration tube, the temperature was raised while stirring under a nitrogen stream over an oil bath of 180° C. After the amine was melted, 10.0 g of hexane-1,3,6-tricarboxylic acid was gradually added, and the contents were stirred at 160° C. for 8 hours. After confirming the disappearance of carboxylic acid by IR, the product was recrystallized from 1.5 L of ethanol, filtered and dried, to obtain 46.9 g of amide compound D (hexane-1,3,6-tricarboxylic acid tri-(3'-octadecyloxypropyl)amide) as a white powdery solid. The yield was 89%. An IR chart and a 400 MHz $^1$H-NMR chart of the obtained compound are shown in FIG. 7 and FIG. 8, respectively.

Example 5

Production of Amide Compound E

Figure 9:
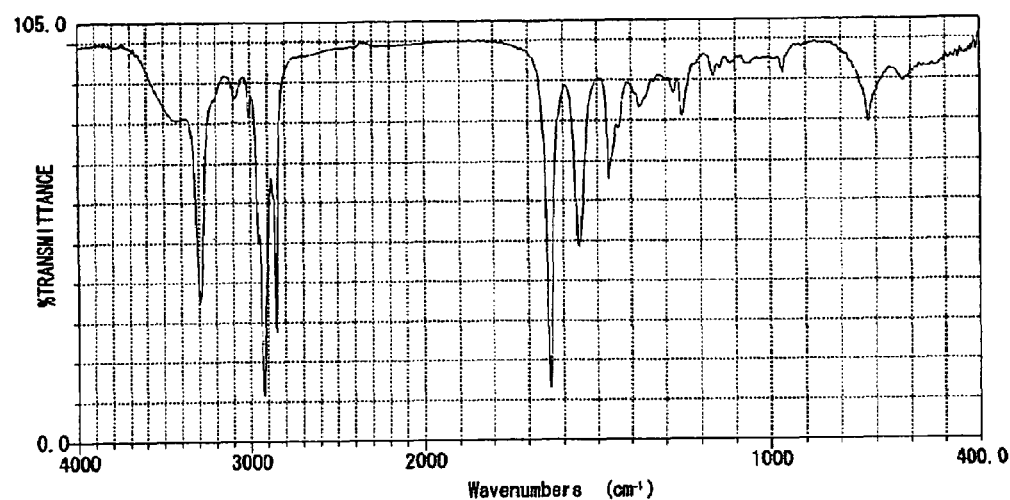
FIG. 9 is an IR chart of the amide compound E obtained in Example 5.
Figure 10:
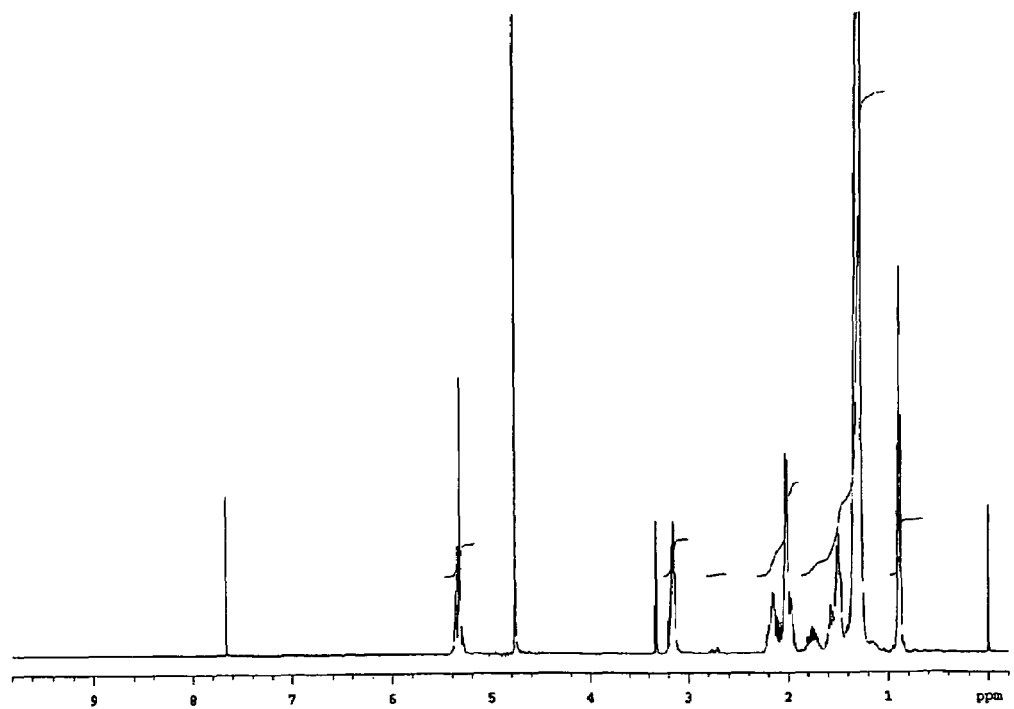
FIG. 10 is a 400 MHz $^1$H-NMR chart of the amide compound E obtained in Example 5.

After charging 82.8 g of oleylamine in a four-necked, round-bottomed 300-mL flask equipped with a dehydration tube, the temperature was raised while stirring under a nitrogen stream over an oil bath of 180° C. When the inner temperature reached 145° C., 15.0 g of hexane-1,3,6-tricarboxylic acid was added and the contents were stirred at 150° C. for 7 hours. The stirring was further continued at 150° C. for 4 hours after adding 27.6 g of oleylamine. After confirming the disappearance of carboxylic acid by IR, the product was recrystallized from 1 L of ethanol, filtered and dried, to obtain 40.5 g of amide compound E (hexane-1,3,6-tricarboxylic acid trioleylamide) as a white powdery solid. The yield was 61%. An IR chart and a 400 MHz $^1$H-NMR chart of the obtained compound are shown in FIG. 9 and FIG. 10, respectively.

Example 6

Production of Amide Compound F

Figure 11:
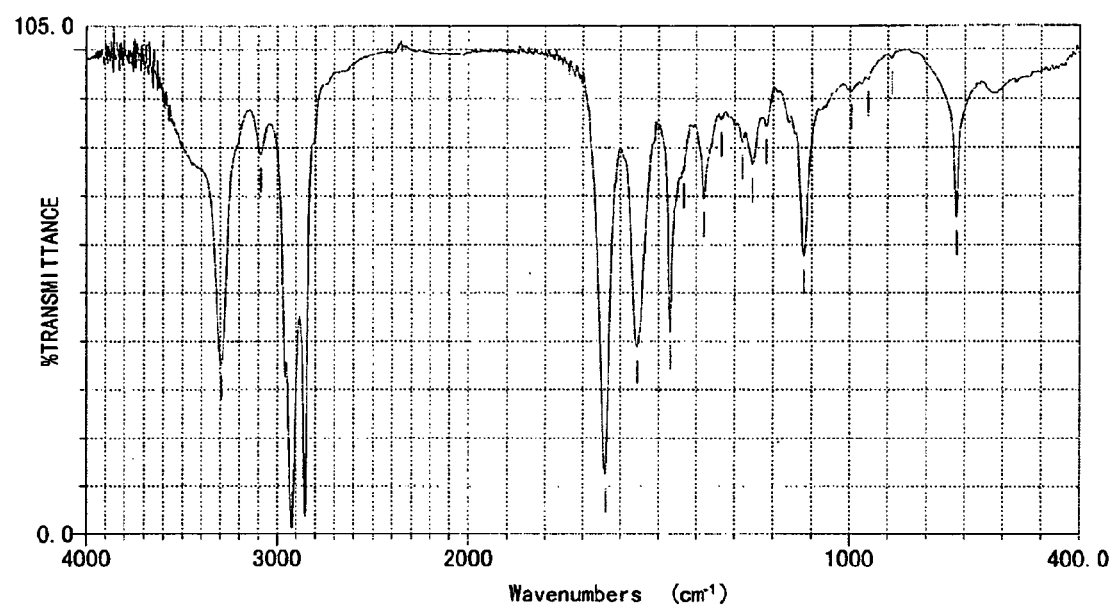
FIG. 11 is an IR chart of the amide compound F obtained in Example 6.
Figure 12:
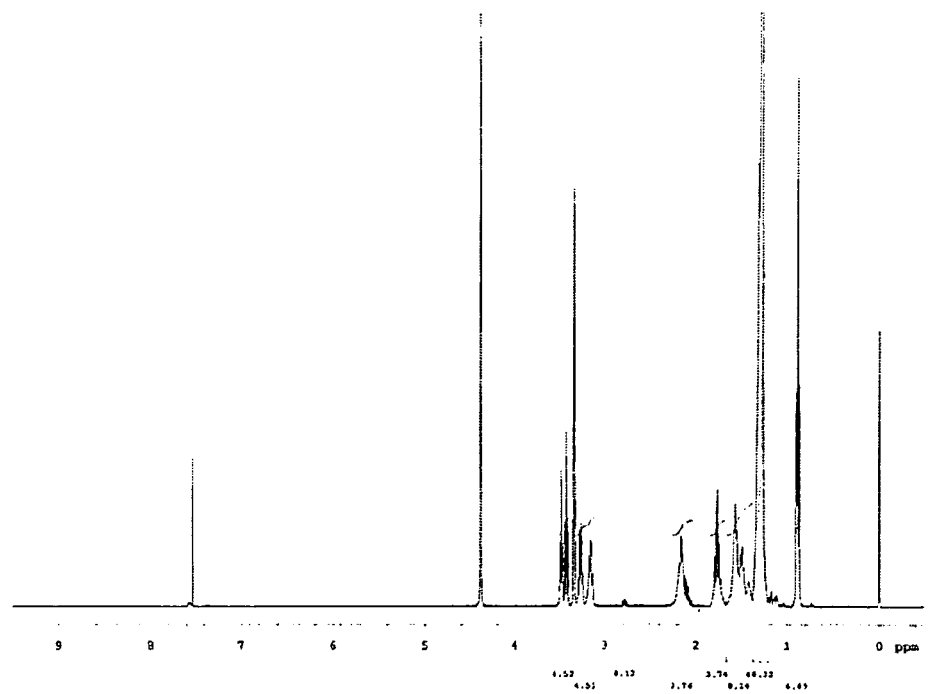
FIG. 12 is a 400 MHz $^1$H-NMR chart of the amide compound F obtained in Example 6.

Into a four-necked, round-bottomed 300-mL flask equipped with a dehydration tube, were charged 152.2 g of 3-octadecyloxypropylamine, 124.7 g of octadecylamine and 50 g of hexane-1,3,6-tricarboxylic acid. The temperature was raised and the contents were stirred at 150° C. for 9 hours under a nitrogen stream while removing the water being generated. After confirming the disappearance of carboxylic acid by IR, the product was recrystallized from 11 kg of ethanol, filtered and dried, and then, repeatedly recrystallized from 6 kg of ethanol, filtered and dried, to obtain 186.9 g of amide compound F (hexane-1,3,6-tricarboxylic acid alkylamide) as a white powdery solid. The 400 MHz $^1$H-NMR measurement showed that 1.5 chains of 3-octadecyloxypropyl group and 1.5 chains of octadecyl group ware introduced in average. The compound was negative for the ninhydrine test, and the yield was 76%. An IR chart and a 400 MHz $^1$H-NMR chart of the obtained compound are shown in FIG. 11 and FIG. 12, respectively.

Example 7

Production of Amide Compound G

Figure 13:
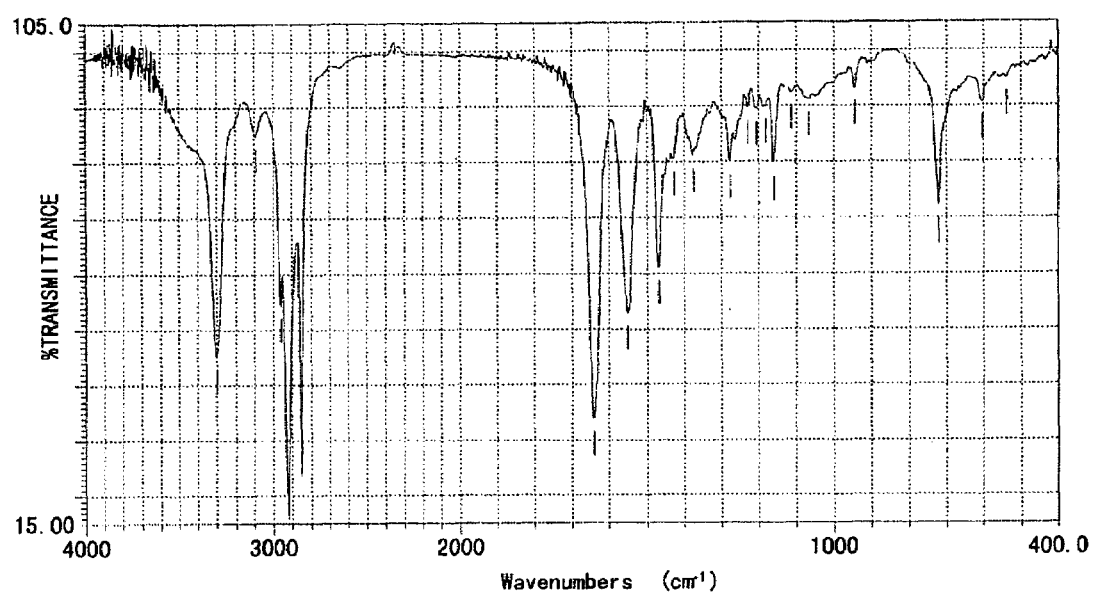
FIG. 13 is an IR chart of the amide compound G obtained in Example 7.
Figure 14:
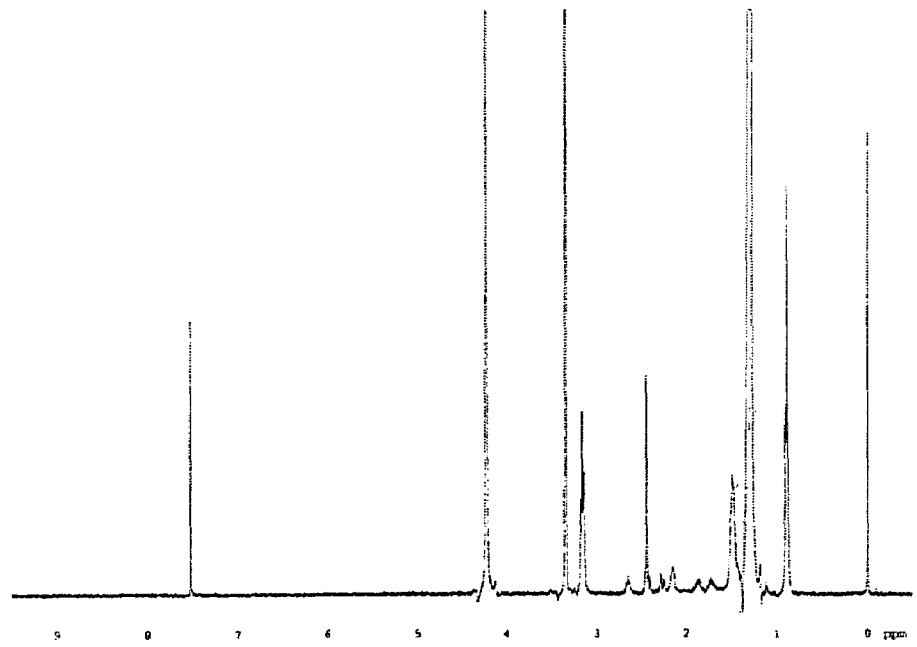
FIG. 14 is a 400 MHz $^1$H-NMR chart of the amide compound G obtained in Example 7.

In a four-necked, round-bottomed 300-mL flask equipped with a dehydration tube, 127.6 g of octadecylamine and 5.0 g of butane-1,2,4-tricarboxylic acid were stirred for 7 hours at 120° C. under a nitrogen stream while removing the water being generated. Thereafter, the product was aged at 150° C. for 15 hours and further at 180° C. for 26 hours. Then, the product was recrystallized twice from a mixed solvent of 1050 g of ethanol and 450 g of chloroform and dried, to obtain 9.5 g of amide compound G (butane-1,2,4-tricarboxylic acid trioctadecylamide) as a white powdery solid. The compound was negative for the ninhydrine test, and the yield was 38%. An IR chart and a 400 MHz $^1$H-NMR chart of the obtained compound are shown in FIG. 13 and FIG. 14, respectively.

Examples 8-15

A mixture of 9.5 g of oily base(s) shown in Table 1 and 0.5 g of each of the amide compounds A to G which had been produced in Examples 1 to 7 was melted while heating over an oil bath of 140° C., and then cooled to room temperature, to obtain each gel composition. Each gel composition thus produced was measured for the gel strength using a compression tester ("KES-G5" manufactured by KES Kato Tech Co., Ltd.) having a cylindrical adaptor (3 mm φ) at a sample plate speed of 0.01 cm/s. Further, each gel composition was visually evaluated for transparency. The results are shown in Table 1.

Comparative Examples 1-2

A mixture of 9.5 g of oily bases shown in Table 1 and 0.5 g of a gelling agent (12-hydroxystearic acid in Comparative Example 1 or N-lauroyl-L-glutamic acid dibutylamide in Comparative Example 2) was treated in the same manner as in Examples 8-15, to obtain each gel composition, which was then measured for the gel strength and visually evaluated for transparency. The results are shown in Table 1 in which each percentage (%) means "% by weight."

TABLE 1

|  | Examples | | | | |
| --- | --- | --- | --- | --- | --- |
|  | 8 | 9 | 10 | 11 | 12 |
| Gelling Agent | | | | | |
| Amide compound A | 5% | | | | |
| Amide compound B | | 5% | | | |
| Amide compound C | | | 5% | | |

TABLE 1-continued

|  | | | | | |
|---|---|---|---|---|---|
| Amide compound D |  |  |  | 5% |  |
| Amide compound E |  |  |  |  | 5% |
| Amide compound F |  |  |  |  |  |
| Amide compound G |  |  |  |  |  |
| 12-hydroxystearic acid |  |  |  |  |  |
| N-lauroyl-L-glutamic acid dibutylamide |  |  |  |  |  |
| Oily Base |  |  |  |  |  |
| Branched hydrocarbon oil (ISOSOL 400K*) | 95% | 57% | 57% | 57% |  |
| Cyclodimethicone (SH245**) |  | 38% | 38% | 38% |  |
| Squalane |  |  |  |  | 95% |
| Isopropyl myristate |  |  |  |  |  |
| Strength (kgf/cm²) | 0.29 | 0.83 | 0.82 | 0.23 | 0.15 |
| Transparency | semi-transparent | transparent | transparent | semi-transparent | transparent |

|  | Examples ||| Comparative Examples ||
|---|---|---|---|---|---|
|  | 13 | 14 | 15 | 1 | 2 |
| Gelling Agent | | | | | |
| Amide compound A |  |  |  |  |  |
| Amide compound B |  |  |  |  |  |
| Amide compound C |  |  |  |  |  |
| Amide compound D |  |  |  |  |  |
| Amide compound E | 5% |  |  |  |  |
| Amide compound F |  | 5% |  |  |  |
| Amide compound G |  |  | 5% |  |  |
| 12-hydroxystearic acid |  |  |  | 5% |  |
| N-lauroyl-L-glutamic acid dibutylamide |  |  |  |  | 5% |
| Oily Base |  |  |  |  |  |
| Branched hydrocarbon oil (ISOSOL 400K*) |  | 57% | 57% | 57% | 57% |
| Cyclodimethicone (SH245**) |  | 38% | 38% | 38% | 38% |
| Squalane |  |  |  |  |  |
| Isopropyl myristate | 95% |  |  |  |  |
| Strength (kgf/cm²) | 0.06 | 0.18 | 1.29 | 0.03 | 0.17 |
| Transparency | transparent | semi-transparent | semi-transparent | opaque | opaque |

*Manufactured by Nippon Petrochemicals Co., Ltd.
**Manufactured by Dow Corning Toray Silicone Co., Ltd.

As seen from Table 1, as compared with the gel compositions prepared in Comparative Examples 1 and 2, the gel compositions of Examples 8-15 are equal or superior to with respect to the gel strength and excellent in transparency.

Example 16 and Comparative Example 3

Using the amide compound C produced in Example 3 (stearyl alcohol in Comparative Example 3 in place of the amide compound C), each stick-type external composition having the composition shown in Table 2 was prepared by the following method. The external compositions were evaluated for the following properties by six professional panelists. Each result is shown in Table 2 by the average value of six evaluation results.

Preparation of External Composition

A 10-mL screw-capped bottle having a magnetic stirrer therein was charged with the amide compound C (stearyl alcohol in Comparative Example 3 in place of the amide compound C), a branched hydrocarbon oil, a cyclodimethicone and an antiperspirant salt in the proportions shown in Table 2. The temperature was raised to 130° C. (80° C. in Comparative Example 3) while stirring, to melt the gelling agent. The melted mixture was poured into a cylindrical hole of 10-mm diameter and 45-mm depth bored in an aluminum mold, and the mold was cooled over a water bath of 20° C. After sufficiently cooling, a stick-type external composition was taken out of the mold.

Methods of Evaluating Properties (1) Hardness

The obtained external composition was applied onto the back of the hand, to evaluate the hardness according to the following criteria.

2: sufficiently hard for a stick-type external composition and no change such as deformation was observed in the stick-type composition during the application except for its surface being in contact with the skin upon application.

1: slightly soft, and a change such as deformation due to the pressure upon the application was observed on the surface being applied.

0: too soft to retain its form.

(2) Easiness of Application

The obtained external composition was applied onto the back of the hand, to evaluate the easiness of application by sensory perception according to the following criteria.

2: well spread and easy to apply.
1: did not spread well and slightly difficult to apply.
0: did not spread and difficult to apply.

(3) Stickiness after Application

The obtained external composition was applied onto the back of the hand, to evaluate the stickiness after application by sensory perception according to the following criteria.
2: not sticky.
1: slightly sticky.
0: very sticky.

(4) White Residue after Drying

The obtained external composition was applied onto the back of the hand. After being allowed to stand for 5 min, the applied portion was visually observed for evaluation according to the following criteria.
2: no white residue.
1. slight white residue.
0: clearly perceivable white residue.

TABLE 2

|  | Example 6 | Comparative Example 3 |
| --- | --- | --- |
| Amide compound C | 300 mg |  |
| Stearyl alcohol |  | 900 mg**** |
| Branched hydrocarbon oil (ISOSOL 400K*) | 2.52 g | 2.16 g |
| Cyclodimethicone (SH245**) | 1.68 g | 1.44 g |
| Squalane | 60 mg | 60 mg |
| Antiperspirant salt (REACH AZP908SUF***) | 1.44 g | 1.44 g |
| Hardness | 2 | 2 |
| Easiness of application | 2 | 0.2 |
| Stickiness after application | 2 | 1 |
| White residue after drying | 2 | 0 |

*Manufactured by Nippon Petrochemicals Co., Ltd.
**Manufactured by Dow Corning Toray Silicone Co., Ltd.
***Manufactured by Reheis, Inc.
****The composition could not be taken out of the mold because of its low hardness when used in an amount of 300 mg or 600 mg.

As seen from Table 1, as compared with the stick-type external composition prepared in Comparative Example 3, the stick-type external composition of Example 16 not only has an equal hardness but also is excellent in the easiness of application, the stickiness after application and the white residue after drying.

Example 17 and Comparative Example 4

Using the amide compound D produced in Example 4 (paraffin wax in Comparative Example 4 in place of the amide compound D), each stick-type cosmetic preparation having the composition shown in Table 3 was prepared by the following method. The cosmetic preparations were evaluated for the following properties by five professional panelists. Each result is shown in Table 3 by the average value of five evaluation results.

Preparation of Cosmetic Preparation

A 10-mL screw-capped bottle having a magnetic stirrer therein was charged with the amide compound D (paraffin wax in Comparative Example 4 in place of the amide compound D), a branched hydrocarbon oil, an ester oil, lanolin, and a pigment in the proportions shown in Table 3. The temperature was raised to 100° C. while stirring to melt the gelling agent. The melted mixture was poured into a cylindrical hole of 10-mm diameter and 45-mm depth bored in an aluminum mold, and the mold was cooled over a water bath of 20° C. After sufficiently cooling, a stick-type cosmetic preparation was taken out of the mold.

Methods of Evaluating Properties (1) Hardness, (2) Easiness of application, and (3) Stickiness after application Each of the above properties was evaluated according to the criteria described in Example 16.

(4) Gloss

The lipstick was visually observed for its appearance and the gloss was evaluated according to the following criteria.
2: good gloss
1: slightly dull gloss
0: poor gloss

TABLE 3

|  | Example 17 | Comparative Example 4 |
| --- | --- | --- |
| Solidifying Agent |  |  |
| Amide compound D | 0.54 g | — |
| Paraffin wax 65° C. min* | — | 0.27 g |
| Paraffin wax 73-80° C.* | — | 0.27 g |
| Oily Base |  |  |
| Vase line | 0.60 g | 0.60 g |
| Anhydrous lanolin** | 0.60 g | 0.60 g |
| Cosmol 222*** | 1.20 g | 1.20 g |
| Estemol N-01*** | 1.80 g | 1.80 g |
| Squalane | 0.60 g | 0.60 g |
| Pigment |  |  |
| Red No. 202 | 0.24 g | 0.24 g |
| Yellow No. 4 Al lake | 0.12 g | 0.12 g |
| Titanium oxide | 0.12 g | 0.12 g |
| Evaluations |  |  |
| Hardness | 2 | 0 |
| Gloss of stick | 2 | 0 |
| Easiness of application | 2 | 1.2 |
| Stickiness after application | 2 | 1.6 |

*Manufactured by Sigma-Aldrich Corporation
**Manufactured by Wako Pure Chemical Industries, Ltd.
***Manufactured by The Nisshin OilliO Group, Ltd.

As seen from Table 3, as compared with the stick-type cosmetic preparation of Comparative Example 4, the stick-type cosmetic preparation prepared in Example 17 is excellent in the hardness, gloss, easiness of application and stickiness after application.

Example 18 and Comparative Examples 5-6

Using the amide compound C produced in Example 3 (N-lauroylglutamic acid α,γ-dibutylamide in Comparative Example 5 and 12-hydroxystearic acid in Comparative Example 6, each in place of the amide compound C), each solid fragrance composition having the composition shown in Table 4 was prepared by the following method. The fragrance compositions were evaluated for the following properties by three professional panelists. Each result is shown in Table 4 by the average value of three evaluation results.

Preparation of Solid Fragrance Composition

A 10-mL screw-capped bottle having a magnetic stirrer therein was charged with the amide compound C (N-lauroylglutamic acid α,γ-dibutylamide in Comparative Example 5 and 12-hydroxystearic acid in Comparative Example 6, each in place of the amide compound C), a branched hydrocarbon oil, cyclodimethicone and a fragrance in the proportions shown in Table 4. The temperature was raised to 140° C. (80° C. in Comparative Example 6 where 12-hydroxystearic acid was used) while stirring, to melt the gelling agent. The melted mixture was poured into a schale of 30-mm diameter and 20-mm depth and cooled at room temperature, to obtain a solid fragrance composition.

Methods of Evaluating Properties (1) Slow Releasability

The fragrance composition was allowed to stand at 24° C. and 78% humidity. The odor strength was evaluated over time by three panelists based on a relative scale of 0 to 5 where 5 was the odor strength during the preparation of the control shown in Table 4 and 0 was odorless (5: control and 0: odorless). The average values of the results are shown in Table 4.

(2) Slow Releasability

The fragrance composition was allowed to stand at 24° C. and 78% humidity, during which the loss in its weight was measured over time.

Loss in weight=1−(measured weight/initial weight)

(3) Appearance

After being allowed to stand at 24° C. and 78% humidity, the fragrance composition was visually observed for its appearance.

TABLE 4

|  | Example | Comparative Examples | | |
|---|---|---|---|---|
|  | 18 | 5 | 6 | Control |
| Gelling Agent |  |  |  |  |
| Amide compound C | 100 mg | — | — | — |
| N-lauroylglutamic acid α, γ-dibutylamide | — | 100 mg | — | — |
| 12-hydroxystearic acid | — | — | 100 mg | — |
| Oily Base |  |  |  |  |
| Branched hydrocarbon oil (ISOSOL 400K*) | 1104 mg | 1104 mg | 1104 mg | 1104 mg |
| Cyclodimethicone (SH245**) | 736 mg | 736 mg | 736 mg | 736 mg |
| Fragrance |  |  |  |  |
| Limonene | 60 mg | 60 mg | 60 mg | 60 mg |
| Odor Strength |  |  |  |  |
| 0 h | 4 | 4*** | 4*** | 5 |
| 4 h | 4 | 4*** | 3*** | — |
| 8 h | 3.7 | 3.7*** | 3*** | — |
| 24 h | 3 | 3 | 2*** | — |
| 48 h | 3 | 3 | 2*** | — |
| Slow Releasability (% by weight) |  |  |  |  |
| 0 h | 0% | 0% | 0% | — |
| 4 h | 2.8% | 3.1% | 4.1% | — |
| 8 h | 5.2% | 5.6% | 7.2% | — |
| 24 h | 14.4% | 15.3% | 18.9% | — |
| 48 h | 27.0% | 28.7% | 31.8% | — |
| Appearance |  |  |  |  |
| 0 h | transparent | opaque | opaque | — |
| 8 h | transparent | opaque | opaque, cracked | — |
| 48 h | transparent | opaque | opaque, cracked | — |

*Manufactured by Nippon Petrochemicals Co., Ltd.
**Manufactured by Dow Corning Toray Silicone Co., Ltd.
***Offensively odorous.

As seen from Table 4, as compared with the fragrance compositions of Comparative Examples 5 and 6, the fragrance composition prepared in Example 18 has an equal or superior slow releasability and is excellent in the aesthetic appearance.

INDUSTRIAL APPLICABILITY

The amide compounds of the present invention have a high ability of gelling oily bases and are useful as a gelling agent for oily bases for use in the cosmetic field and other fields. The gelling agents of the invention containing such an amide compound exhibit a strong gel strength and provide gel compositions with a good transparency. Such gel compositions are usable as cosmetic preparations in the form of a gel cosmetic preparation, pack cosmetic preparation, powder cosmetic preparation, etc. and also usable as external compositions for skin and fragrance compositions.

What is claimed is:

1. An amide compound represented by the following formula 1:

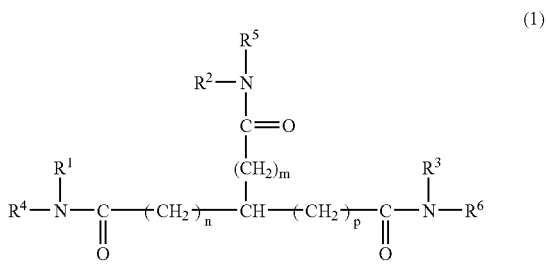

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group; and m is 2, n is 0 and p is 3.

2. A gelling agent comprising an amide compound represented by the following formula 1:

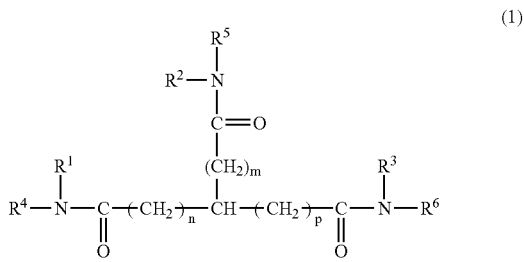

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group; wherein m is 2, n is 0, and p is 3, or m is 1, n is 0, and p is 2.

3. A gel composition comprising an oily base and the gelling agent as defined in claim 2.

4. An external composition comprising an amide compound represented by the following formula 1:

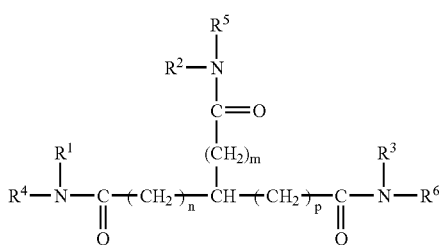

(1)

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^2$ and $R^3$ are each independently a saturated or unsaturated, linear or branched hydrocarbon group having a total carbon number of from 6 to 24 which optionally has at least one group selected from the group consisting of an ether group, amide group, ester group, amino group and hydroxyl group: wherein m is 2, n is 0, and p is 3, or m is 1, n is 0, and p is 2.

5. A cosmetic composition comprising an amide compound represented by the following formula 1:

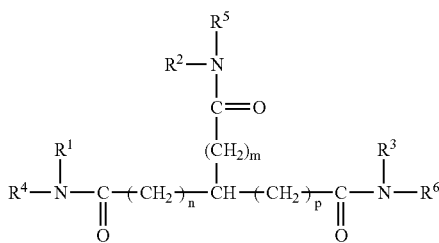

(1)

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group: wherein m is 2, n is 0, and p is 3, or m is 1, n is 0, and p is 2.

6. A fragrance composition comprising a fragrance and an amide compound represented by the following formula 1:

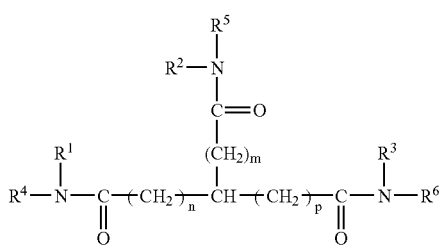

(1)

wherein $R^1$, $R^2$ and $R^3$ are each independently a hydrogen atom or an alkyl group having a carbon number of from 1 to 3 with the proviso that at least one of $R^1$, $R^2$ and $R^3$ is a hydrogen atom; $R^4$, $R^5$ and $R^6$ are each independently a saturated or unsaturated, linear or branched hydrocarbon group having a total carbon number of from 6 to 24 which optionally has at least one group selected from the group consisting of an ether group, amide group, ester group, amino group and hydroxyl group: wherein m is 2, n is 0, and p is 3, or m is 1, n is 0, and p is 2.

* * * * *